US005744657A

United States Patent [19]
Webster

[11] Patent Number: 5,744,657
[45] Date of Patent: Apr. 28, 1998

[54] PROCESS FOR THE PREPARATION OF PERFLUOROCARBONS

[75] Inventor: James Lang Webster, Parkersburg, W. Va.

[73] Assignee: E. I. du Pont de Nemours and Company, Wilmington, Del.

[21] Appl. No.: 573,828

[22] Filed: Dec. 18, 1995

Related U.S. Application Data

[63] Continuation-in-part of Ser. No. 540,352, Oct. 6, 1995, abandoned, which is a continuation-in-part of Ser. No. 362,321, Dec. 22, 1994, abandoned.

[51] Int. Cl.⁶ .................................................. C07C 19/08
[52] U.S. Cl. .......................................... 570/150; 570/142
[58] Field of Search ..................................... 570/150, 142

[56] References Cited

U.S. PATENT DOCUMENTS 4,087,475  5/1978  Jordan ...................................... 570/150
4,962,247  10/1990  Holbrook ................................. 570/150

*Primary Examiner*—Alan Siegel

[57] ABSTRACT

Tetrafluoroethylene and other valuable 2-carbon atom fluorocarbon is made by reacting fluorine-containing compound such metal fluoride with CO in an energized state, e.g. plasma excitation, to form a gaseous reaction mixture which is a precursor to $COF_2$, followed by reacting this reaction mixture with carbon and quenching to obtain the desired fluorocarbon.

36 Claims, No Drawings

PROCESS FOR THE PREPARATION OF PERFLUOROCARBONS

This application is a continuation-in-part of U.S. patent application Ser. No. 08/540,352 filed Oct. 6, 1995 now abandoned, which is in turn, a continuation-in-part of U.S. patent application, Ser. No. 08/362,321, filed Dec. 22, 1994 now abandoned, all by the same inventor.

FIELD OF THE INVENTION

This invention relates to the synthesis of such perfluorocarbons as tetrafluoroethylene.

BACKGROUND OF THE INVENTION

The term "perfluorocarbon" as used herein refers to compounds containing carbon and fluorine, wherein all of the substituents on the carbon atoms are fluorine. Thus, this term includes the unsaturated perfluorocarbons, notably the perfluoroolefins, such as tetrafluoroethylene.

U.S. Pat. No. 2,902,521 (Cleaver et al.) is one of many early patents disclosing the synthesis of perfluorocarbons such as tetrafluoroethylene (TFE). This particular patent disclosing the reaction between organic or inorganic fluoride with carbon at elevated temperature in the presence of at least 0.2 mol % of oxygen per mol of fluoride and sufficient carbon present to combine with all the added oxygen and to form TFE. The reaction between the oxygen and carbon is exothermic and as such, is disclosed to provide part of the heat needed for the reaction temperature. Thus, the patent discloses the existence of two concurrent reactions: fluorination of carbon and oxidation of carbon. Carbon monoxide is detected in the gaseous reaction product, as a carbon/oxygen reaction product. The results of this process as disclosed in the Examples is to obtain TFE and other fluorocarbons as the major reaction products, e.g., Example V discloses the presence of 25 mol % TFE and 11 mol % carbon tetrafluoride in the reaction product. Such processes involving carbon as a reactant had numerous disadvantages, resulting in such processes never achieving commercial exploitation.

Instead, TFE and related fluorocarbons have been made commercially since the 1950's by TFE manufacturers worldwide by an entirely different process, involving (i) the reaction of $CaF_2$ with $H_2SO_4$ to form HF, (ii) the reaction of HF with chloroform to form chlorodifluoromethane (HCFC-22), (iii) pyrolysis of F-22 to form TFE and related fluorocarbons such as hexafluoropropylene (HFP), and (iv) refining the TFE, i.e., separating it from the other fluorocarbon reaction products and unreacted HCFC-22, so that it is useful as a monomer for polymerization to make such products as polytetrafluoroethylene and tetrafluoroethylene copolymer plastics and elastomers. While achieving high yield of desired product, this process has the disadvantage of requiring very high plant investment. The process basically involved the building of four plants, one to make the HF, one to make the chloroform reactant, one to make the HCFC-22, and one for pyrolysis/refining. This process has also involved the additional disadvantage of requiring the disposal of large amounts of HCl.

There has existed a long-felt need to be able to synthesize perfluorocarbons, notably TFE, both economically and at high yield.

SUMMARY OF THE INVENTION

The present invention satisfies this need. A simplified statement of the process satisfying this need is first, reacting metal fluoride with carbon monoxide (CO) to form carbonyl fluoride ($COF_2$) and second, reacting this $COF_2$ with carbon to form primarily perfluorocarbon, such as TFE, which contains at least two carbon atoms. In greater detail, the process can be described as a process for the preparation of perfluorocarbon (at least one) containing at least two carbon atoms, comprising feeding fluorine-containing compound having a molecular weight greater than 20 and gaseous CO to a reaction zone wherein the fluorine-containing compound is split apart to liberate fluorine from said fluorine-containing compound and obtaining a gaseous reaction mixture which contains said fluorine and said CO, reacting said reaction mixture with carbon to obtain a gaseous reaction product, rapidly cooling said gaseous reaction product to obtain said perfluorocarbon as a result thereof, and recovering said perfluorocarbon from said gaseous reaction product.

The preferred fluorine-containing compound is metal fluoride. Under the preferred condition, the liberation of fluorine from the fluorine-containing compound or metal fluoride is accomplished in the presence of heat providing an elevated temperature within the reaction zone. The fluorine and CO are maintained as such, rather than the metal recombining to form metal fluoride, by cooling the gaseous reaction mixture. This may cause the metal to solidify, enabling its separation from the gaseous reaction mixture, whereby the fluorine is less able to recombine with the metal. Alternatively, the metal can be included in the reaction mixture which is reacted with carbon at elevated temperature, and the perfluorocarbon is thereafter recovered (separated) from the metal as well as from the remainder of the gaseous reaction product.

In still greater detail, the process for the preparation of perfluorocarbon containing at least two carbon atoms comprises (a) feeding metal fluoride and gaseous CO to a reaction zone in which the feed materials are energized to cause the metal fluoride to split apart and form a gaseous reaction mixture containing one or more reaction products, including metal from said metal fluoride and the combination of CO and fluorine from said metal fluoride, and unreacted feed material, (b) maintaining said combination of CO and fluorine from said metal fluoride by (i) cooling said reaction mixture from the high temperature in said reaction zone resulting from the energizing of said feed materials and/or (ii) removing said metal from said reaction mixture, (c) reacting said combination of CO and fluorine in said reaction mixture with carbon, (d) removing said metal from said reaction mixture prior to step (c) if not already removed under step (b) if the presence of said metal in the reaction mixture would adversely affect step (c), (e) rapidly cooling the gaseous reaction product from step (c) to obtain the perfluorocarbon as a result thereof, and (f) recovering said perfluorocarbon from the resultant reaction product.

In a preferred embodiment, the energizing of the feed materials is done by plasma excitation which generates extremely high temperatures, e.g., thousands of degrees centigrade, at which temperature the identity of the reaction product is essentially unknown, but which identity becomes known by quenching the gaseous reaction mixture to a temperature at which a stable compound, which is preferably COF$_2$, is present. Thus, the reaction mixture is capable of being quenched to form COF$_2$ and is therefore a precursor to COF$_2$.

In another preferred embodiment, the process is conducted continuously so that the fluorine-containing compound such as metal fluoride and CO are the feed materials at the beginning of the process and carbon is the feed material into the intermediate step (step (c)) and the perfluorocarbon is recovered from the output of the process.

Step (a) together with step (b) is thermodynamically not a favored reaction, because the fluorine atoms and the metal tend to reunite, but the energizing of the feed materials, typically by high temperature and/or an electrically charged environment in the reaction zone, such as is available from plasma equipment, drives the reaction, causing the metal fluoride-containing compound such as metal fluoride to split apart. As stated above, the tendency of the resultant dissociated fluorine and metal tending to recombine can be avoided by rapidly cooling the resultant gaseous reaction mixture to bind up the fluorine with CO moiety. In addition or alternatively, the metal can be made unavailable to the fluorine, such as by the cooling step causing the metal to liquefy or solidify, making it easily separable from the gaseous reaction mixture, and then removing the metal from the reaction mixture.

In another preferred embodiment, at least a portion of the energization heat used to drive the reaction of step (a) is also used to drive the reaction of step (c).

The reaction of step (a) together with step (b) consumes CO, and in a preferred embodiment the reaction of step (c) produces CO. Preferably the CO produced in step (c) is recycled to become a feed material for at least a portion of the CO feed to step (a). This provides productive use in the same manufacturing site for this toxic material. In the most preferred embodiment, the CO formed in step (c) forms essentially the entire CO feed to step (a), whereby the fluorine-containing compound is essentially the only new externally supplied consumable feed material to step (a). In accordance with this preferred embodiment, most of the externally supplied consumable feed materials to-the entire process are fluorine-containing compound such as metal fluoride in step (a) and carbon in step (c).

The process of the present invention provides the following advantages: The fluorine-containing compound such as metal fluoride starting material can be inexpensive, especially relative to the cost of HCFC-22. A single manufacturing plant of relatively low investment can be used. No HCl is produced in the process of the present invention, which simplifies the refinement of the perfluorocarbon and avoids the disposal problem for HCl. The desired perfluorocarbon can be produced in high yield. The metal of the metal fluoride can be recovered (step (b)), its value further contributing to the economy of the process of the present invention.

DETAILED DESCRIPTION OF THE INVENTION

With respect to the starting materials of the process of the present invention, the CO can be obtained commercially or it can be created in situ by feeding O$_2$ and C to the reactor, preferably with the conversion to CO being completed prior to contact with the fluorine-containing compound, so that oxygen from the oxygen feed is no longer present for reaction with any portion of the fluorine-containing compound. Any compound which provides fluorine to the reaction with CO can be used. Preferably, however, the compound is free of hydrogen and any other halogen atom. The requirement that the compound have a molecular weight of greater than 20 excludes HF as a suitable compound. Since F$_2$ is not a compound, it too is excluded as a feed material to the reactor. The compound-serving as the source of fluorine can be organic or inorganic, the latter being preferred because inorganic compounds are naturally occurring or are obtained by processing naturally occurring compounds, wherein the fluorine-containing compound may be a by-product of such processing and will typically be non-carbonaceous. Organic fluorine-containing compounds may also have by-product sources, and indeed, could be from the recycle by-product stream obtained from the process of the present invention.

The fluorine-containing compound can be a compound or a mixture of compounds, i.e., at least one fluorine-containing compound. It is the fluorine atoms that are the reactive portion of the compound, whereby the remaining portion of the compound can have a wide range of identities. It is only necessary that the fluorine-containing compound provide fluorine to the reaction, which is generally accomplished by the compound liberating fluorine under reaction conditions involving heat. With respect to metal fluoride as the preferred fluorine-containing compound, the metal can be selected from elements in Groups IA, excluding hydrogen, IB, IIA, IIB, IIIA, IIIB, IVA, VA, excluding nitrogen, VB, VIA, excluding oxygen, VIB, VIIB, and VIII of the Periodic Table (R. H. Perry and C. H. Chilton, *Chemical Engineers' Handbook*, 5th Edition, McGraw-Hill, inside cover (1973)). Preferably, the metal portion of the metal fluoride has inertness or low reactivity to the CO reactant under the conditions of the reaction and the reaction conditions are such that the fluorine atoms which leave the fluorine-containing compound during the reaction do not return. Such reaction conditions can include rapid cooling of the reaction mixture so that the fluorine split off from the fluorine-containing compound more stably combines with the CO moiety so as to be unavailable to return. The fluorine-containing compound, including metal fluoride, can be simple or complex, e.g., containing two cations and one anion, such as fluorine-containing complex salts. Examples of metal fluorides include sodium fluoride, magnesium fluoride, and sulfur fluoride. Preferred fluorides because of low cost include CaF$_2$ and silicon fluoride such as SiF$_4$, Si$_2$F$_6$, and metal silicon fluorides (fluorosilicates) such as calcium fluorosilicate. Additional metal fluorides include fluoroborates, fluorophosphates, and cryolite (Na$_3$AlF$_6$) Examples of organic fluorides include CF$_4$, C$_2$F$_6$, and perfluoroolefins such as tetrafluoroethylene and hexafluoropropylene depending on the perfluorocarbon desired.

The reaction between fluorine-containing compound and CO feed materials, however obtained, includes the removal of the fluorine atoms from the fluorine-containing compound. Thermodynamically, as an equilibrium reaction, the reformation of the fluorine-containing compound such as metal fluoride is generally to be expected. To make the dissociation reaction occur, however, the reactants are exposed to sufficient energy which is effective to energize the feed material, i.e., to cause dissociation of at least a portion of at least one of the reactants in the reaction zone. This dissociation can be into radicals, atoms, and/or ions, which in essence is the excited state for the molecules of the feed material. In a sense, the reaction is being initiated by dissociation energy being present in the reaction zone. Although the reaction may be occurring between radicals, atoms, and/or ions, the reaction can simply be described as the reaction between the fluorine-containing compound such as metal fluoride and CO. The effect of the excited state of the feed material is that the fluorine from the fluorine-containing compound combines with the CO in some way in the gaseous reaction mixture. Measures to maintain this combination so that the fluorine does not recombine with the remainder of the compound such as the metal will be described later herein.

The description of the present invention herein having revealed the starting materials and reaction mechanism to be used, one skilled in the art will recognize many ways to expose (subject) the reactants to the dissociation energy required. Thus, the reaction can be carried out by producing the dissociation energy by an electrical arc, either A.C. or D.C., using a plasma reactor or by other equipment which produces electromagnetic energy, such as an induction coil. In the case of the electric arc, the applicator of the dissociation energy is within the reaction zone, while in the case of the induction coil, the applicator of the electromagnetic energy can be exterior to the reaction zone, but creating the dissociation energy within the zone.

A plasma reactor is one type of apparatus for carrying out the metal fluoride/CO reaction by plasma excitation. This type of energy generator includes a pair of electrodes which generates an arc from electrical current passing from one electrode to the other. An electrical discharge between these electrodes can be rotated by a coil-induced magnetic field or the arc can be stationary. The electrodes can be of copper and water cooled so as to provide long operating time. It is the region of the arc that provides the dissociation energy useful in the present invention; in this case both electrical energy and the thermal energy are generated by the electrical current. The arc region produces a plasma of material fed to it and which dissociates upon exposure to the arc, and this in turn can produce a glow region extending downstream from the arc, in the direction of the fluid flow within the reactor, which glow area is called the plasma flame. The temperature produced by the arc can be controlled by varying the arc power input and/or material feed rate. For the particular power available from the reactor, the flow rate of the feed material is adjusted so that the feed material becomes energized (excited) by this exposure to dissociation energy. Measures can be taken, e.g., a rotating electric arc, to produce a turbulent mixing action in the reaction zone and within the arc, to give high operating efficiency and prolonged electrode life.

Each of the feed materials can be directly or indirectly energized, i.e., exposed (subjected) to the dissociation energy generated by the electric arc or by other means. An example of direct exposure would be when all of the reactants are fed to the electric arc (or the electromagnetic field of different apparatus). An example of indirect exposure would be when only one of the reactants is in the arc (direct exposure), and the resultant dissociated reactant is then brought into contact with the other reactant (indirect exposure) downstream from the arc, within the plasma flame Another example of indirect exposure would be when an inert gas such as argon is directly exposed to the arc or electromagnetic field to cause a portion of the argon to dissociate, and the resultant argon is then brought into contact with the reactants. The plasma flame is formed from the particular feed material that is directly exposed to the arc in the plasma reactor but the flame may also envelop the feed material(s) brought into contact with the plasma downstream from the arc. Thus, the present invention includes all of these possibilities for exposing the feed materials to dissociation energy (energizing of the feed materials) in the reaction zone or as stated above, energizing the feed material going to step (a) of the process. These possibilities can be effective to prolong electrode life in the case when one or more of the feed materials are corrosive to the electrode. Thus CO may be the only reactant fed to the electrode region, or inert gas such as argon may be fed to the electrode region instead on any of the reactants. The reaction zone includes the region of the electric arc or electromagnetic energy in which the plasma is developed and the region in which the feed materials are brought together.

The combination of electrical and thermal energy used to energize the feed material can generally be quantified by specification of the power input to the reaction. Thermal energy may also be provided by preheating one or more of the materials fed to the reaction zone.

The temperature in the electric arc or electromagnetic field will be varied by varying power input and/or feed material flow rate depending on the particular fluorine-containing compound reactant and pressure within the reaction zone to cause the formation of a plasma flame. In the case of metal fluoride reactants, fluorine is most tightly bound to such metals as silicon, magnesium, calcium, and aluminum, and less so to metals such as iron, copper, zinc, and silver. In general, less energy (lower temperature) is required to dissociate the metal fluoride when the metal/fluorine bond is weaker. For any particular metal fluoride, lower pressure within the reaction zone allows the dissociation to occur at lower temperature. The pressure can be sub-atmospheric, atmospheric, or super-atmospheric. By way of example of the effect of pressure, if carbon tetrafluoride were fed to the reaction zone, the level of dissociation at atmospheric pressure and 2700° C. would be similar to that obtained at 10 mm Hg and 2200° C.

For the range of fluorine-containing compounds, e.g. starting materials that can be used, along with the range of pressures that can be used, it is believed that when heat is present in the creation of the dissociation energy, the temperature where the reactants come together in the reaction zone will be sufficient to liberate fluorine from the fluorine-containing compound, generally at least 1500° C. at atmospheric pressure, but lower temperatures may be used at subatmospheric pressures. More often, the temperature will be at least 3500° C. and preferably at least 4500° C. at atmospheric pressure. Extremely higher temperatures may be used, e.g., even more than 10,000° C., at which temperature, all reactants could be dissociated. At such temperatures, the fluorine-containing compound, e.g. metal fluorides, if not gaseous at ambient temperature, are either completely or partially volatilized in the reaction zone. The temperature to which the fluorine-containing compound, such as metal fluoride, is exposed in the reaction zone may be sufficient to cause the metal fluoride to dissociate into metal ions and fluoride ions, but may or may not cause substantial dissociation of the CO. The metal fluoride or other fluorine-containing compound may be exposed to a higher temperature in the reaction zone than the CO by having the metal fluoride be exposed to the maximum dissociation energy present (the arc in the case of a plasma reactor) and then bringing the at least partially dissociated metal fluoride into contact with the CO at a lower temperature, e.g., within the plasma flame created by the energized metal fluoride.

The temperature of the plasma flame decreases with increasing distance from the source of the flame, e.g., the plasma torch. Introduction of the CO reactant to the flame downstream from the torch and the point(s) of introduction of the fluorine-containing compound to the flame provides for reaction of the CO with dissociating fluorine-containing compound, but essentially no dissociation of the CO reactant. Depending on the temperature of the flame at the point of CO introduction and the amount of CO introduced, the CO may also quench the plasma flame while simultaneously reacting with fluorine from the dissociated fluorine-containing compound. Preferably, the CO is less than 20% dissociated, more preferably, less than 10% dissociated, and even more preferably is almost entirely molecular CO at the time of reaction.

Silicon tetrafluoride is gaseous at ambient conditions and thus provides a convenient feed to the reaction zone, wherein both reactants fed to the reaction zone are gaseous. $CaF_2$, e.g., boils at 2500° C. and can therefore be present as a gas or mixture of gas and solid or liquid in the reaction zone, depending on the temperature and pressure in this zone. The metal fluoride or other fluorine-containing compound may even be present as a mixture of gas and solid material, again depending on the particular or other fluorine-containing compound, but preferably the reactants are all gaseous under the conditions of the reaction. Temperatures of about 2000° C. and less can conveniently be measured with a thermocouple. Higher temperatures, especially those of an electrical arc or plasma flame can be determined by known means, such as is determined from such parameters as power inputs, feed compositions, flow rates, and measurement of heat losses or as determined from emission spectroscopy.

The proportion of CO in the feed to the reaction zone is preferably sufficient to combine with the fluorine atoms of the fluorine-containing compound so that fluorine atoms are not left over to recombine with the metal to re-form metal fluoride. This is not to say that all of the fluorine-containing compound fed to the reaction zone will react with the CO in a single pass through this zone. It may be desirable to react only a portion of the fluorine-containing compound in a single pass through the zone and to recycle unreacted fluorine-containing compound to the reaction zone for further conversion. Preferably, however, the reaction is conducted so that a single pass is sufficient, wherein at least 50% of the metal fluoride as other fluorine-containing compound is stripped of its fluorine and more preferably, at least 85%, and even more preferably, at least 90%. These conversions can also be obtained by recycling of unreacted metal fluoride or other fluorine-containing compound.

The principle reaction products present as a gaseous reaction mixture from the metal fluoride (or other fluorine-containing compound)/CO reaction are believed to be metal (or other moiety of the fluorine-containing compound) and some combination of F and CO. Thus the reaction might be depicted by the following equation:

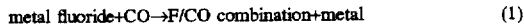

metal fluoride+CO→F/CO combination+metal     (1)

Other fluoride-containing compound may be substituted in whole or in part for the metal fluoride. At the temperature of the dissociation of the metal fluoride (or other fluoride-containing compound), the combination of F and CO has not been identified, i.e., it is uncertain whether the F is combined with part or all of the CO moiety or are present as a dissociated entity. When the reaction mixture is rapidly cooled, the predominant species can be $COF_2$ and $CF_4$, but the predominance of $COF_2$ is preferred. The presence of excess CO drives the process towards the production of $COF_2$ (when rapidly cooled) rather than allowing (thus preventing) the fluorine to react with the metal to reform metal fluoride. Since CO is generally more thermally stable than metal fluorides or other fluoride-containing compound, atmospheric pressure and higher pressure tends to drive the combination of F and CO to favor the formation of $COF_2$ rather than $CF_4$. The presence of $COF_2$ and $CF_4$ at some point in the gaseous reaction mixture is deduced from the presence of $COF_2$ and $CF_4$ as reaction products upon the rapid cooling (quenching) of the reaction mixture to a temperature which is less than 500° C., as being the dominant fluorinated material present, e.g., the yield of $COF_2$ is at least 60%, based on the conversion of metal fluoride or other fluorine-containing compound, preferably at least 80% and more preferably at least 90%. $COF_2$ or the combination of F and CO in the reaction mixture which tends towards $COF_2$ formation (as confirmed by quenching) is the preferred reaction product because it contains oxygen, which is then not available for reacting with the metal to form oxide and is the preferred starting material feed along with carbon to the reaction of step (c). Any $CF_4$ which may be formed is thought to come from free carbon made available by dissociation of CO into carbon and oxygen. Such oxygen is also available to react with the metal formed.

Preferably at least one molecule of CO is present in the feed to the reaction zone for each two atoms of fluorine present and more preferably at least 4 molecules of CO are present/two fluorine atoms. A large excess of CO can be present, e.g., up to 20 molecules CO/two fluorine atoms. The presence of large excesses of CO increases the need for generation of more heat (power) to energize the feed material, and thus can increase the cost of the process.

The gaseous reaction mixture in addition to containing the combination of F and CO and metal in gaseous form as reaction products, may also contain at least one of the following: unreacted metal fluoride or other fluorine-containing compound, unreacted CO, and small amounts of byproducts, e.g., metal oxide. The gaseous reaction mixture may also have present non-gaseous material in case the metal fluoride or other fluorine-containing compound was not completely vaporized in the reaction zone.

Care should be taken to prevent the fluorine in the reaction mixture from reacting with the metal (or other fluorine-containing compound) present to reform metal fluoride. The use of excess CO has already been discussed. Maintenance of the F/CO combination can be furthered by rapid cooling of the reaction mixture to a temperature at which the fluorine either becomes bound to the CO moiety, e.g., as $COF_2$, or the reactivity of the fluorine for the metal (or other moiety) is greatly reduced or both. The rapidity of the cooling desired will depend on the tendency of the F to react with the metal (or other moiety) and this rapid cooling can be obtained, e.g., by bringing the reaction mixture into contact with a cooled surface and/or by mixing with a gas supplied at ambient temperature. This cooling of the reaction mixture can also cause the metal or other moiety) to liquefy or solidify, which not only reduces its reactivity with F, but enables the metal to be separated from the still gaseous reaction mixture. With the metal removed from the reaction mixture, the F can no longer react with the metal (or other moiety). Unreacted metal fluoride and liquefying or solidifying byproducts such as metal oxide may also be removed at this point along with the metal and recycled to step (a).

In one embodiment of the present invention, the reaction mixture is cooled to the temperature of the reaction of step (c). In this embodiment, the reaction mixture fed to step (c) may include metal byproduct (or other moiety) in gaseous form. In another embodiment, the reaction mixture is cooled to a lower temperature which is sufficient for the metal (or other moiety) and byproducts to become non-gaseous for easy removal from the reaction mixture, and then reheated to the reaction temperature desired for step (c). In both of these embodiments, heat recovered from steps (a) and (b) satisfies at least part of the heat requirement for step (c), and the process involving steps (a) and (c) is continuous. In these embodiments, it is preferred to quench the reaction mixture to a temperature less than 2000° C., so that the F/CO combination favors $COF_2$, but the temperature may be maintained above 1500° C. so as to retain as much heat as possible for the reaction of step(c) when the fluorine present does not react to reform the metal fluoride or other fluoride-containing compound. In still another embodiment, the reaction mixture is cooled rapidly to a temperature less than 5000° C., e.g., to ambient temperature, to obtain primarily $COF_2$ and possibly a small amount of $CF_4$, which reaction products can serve as the feed material along with carbon to step (c) in either a continuous or discontinuous process with respect to the performance of step (a). In still another embodiment, the reaction mixture is quenched to a temperature of 500° C. to 2000° C. Cooling in this and other embodiments should be carried out rapidly to obtain the maximum amount of $COF_2$, e.g., at a quench rate of at least 1000° C./sec and more preferably at a rate of at least 10000° C./sec, e.g., 100,000° C./sec and 1,000,000° C./sec.

The next reaction step, step (c), in accordance with the process of the present invention is to react at least the F/CO combination in the reaction mixture described above with carbon to form the desired perfluorocarbons, primarily those which contain at least two carbon atoms, although small amounts of one-carbon-atom perfluorocarbon might also be formed, e.g., $CF_4$. Among the desired perfluorocarbons are fluoroolefins such as tetrafluoroethylene and hexafluoropropylene, and perfluoroalkanes such as hexafluoroethane. The present invention can obtain a yield of at least 2-carbon-atom perfluorocarbons of at least 30% and preferably at least 70%, and more preferably at least 90%.. These yields are with reference to the starting metal fluoride or other fluorine-containing compound and are applicable to single-pass processes and to recycle processes (ultimate yield), and to specific groups of the perfluorocarbons and to specific perfluorocarbons, e.g., perfluoroolefins as a specific group and tetrafluoroethylene as a specific perfluoroolefin.

In case the vaporized metal (or other moiety) present in the gaseous reaction mixture would become non-gaseous under the condition of the reaction step with carbon or eventual recovery of the desired fluorocarbon, and/or if non-gaseous material were present in the gaseous reaction mixture, it is preferred to separate such material prior to the carbon reaction step. This separation step is desirable, particularly in the case of metal which would eventually liquefy and solidify upon cooling, threatening to clog the apparatus used for the carbon reaction step. When the metal is silicon, its purity can be high, making this a valuable byproduct of the process of the present invention. The use of elevated pressure in the reaction zone, minimizes the dissociation of CO, which in turn, minimizes the availability of oxygen being present to form silicon dioxide, which would be a contaminant in the silicon metal byproduct. Additional non-gaseous material can be separated from the gaseous reaction mixture, along with the metal, such as unreacted metal fluoride or other fluorine-containing compound and any metal oxide byproduct, by conventional means. For example, the reactor may be a vertically oriented equipment wherein the non gaseous products would in essence fall out of the bottom of the reactor.

When the metal fluoride/CO reaction is carried out at a temperature higher than the carbon reaction, the metal may be recovered from the gaseous reaction mixture by quenching the reaction mixture as described above to the liquefying or solidifying temperature of the metal products (metal, metal fluoride, metal oxide, if any) thus allowing easy separation from the remaining gaseous mixture. As reference points, the boiling point of silicon is about 2350° C., calcium is 1480° C., calcium fluoride is 2500° C., silicon tetrafluoride is −86° C., and silicon dioxide is 2330° C. Melting points of these materials are as follows: silicon 1410° C., calcium 840° C., calcium fluoride 1420° C., silicon tetrafluoride −90° C. and silicon dioxide 1720° C. When the presence of the metal (or other moiety) would not adversely affect the carbon reaction and may have value not worth recovering, the separation step can be omitted.

The carbon reaction step, carried out on the remainder of the gaseous reaction mixture, can be carried out as a continuation of the metal fluoride (or other fluorine-containing compound)/CO reaction step, i.e., without interruption, or the remainder of the reaction mixture can be cooled and inventoried for subsequent reaction with carbon. The former is preferred because the heat present in the reaction mixture can be used to supply some or most of the heat required for the reaction with carbon.

The reaction between the remainder of the reaction mixture and carbon will generally be carried out to form a second gaseous reaction mixture at a temperature of at least 1500° C. and more often at least 1700° C., depending on pressure used, whether pressure be sub-atmospheric, atmospheric, or super-atmospheric. The apparatus and the form of the carbon used can vary widely, with the objective of obtaining intimate contact between the solid carbon and the remainder of the gaseous reaction mixture. Reaction temperatures higher than 3000° C. are believed to be unnecessary. In a preferred embodiment, the reaction is carried out by reacting the gaseous reaction mixture with the carbon (solid particles) at 2400° C. to 2800° C. and atmospheric pressure to form the desired perfluorocarbons. The reaction product from this reaction is quenched to obtain these perfluorocarbons, usually with TFE predominating, and possibly accompanied by lesser amounts of HFP and hexafluoroethane. Staged quenching or slower quench rates, e.g., 10000° C./sec, can favor the formation of hexafluoropropylene and hexafluoroethane compared to TFE.

Thus the carbon reaction upon quenching can be depicted as follows:

$$F/CO+\text{combination}+C \rightarrow \text{perfluorocarbon}(C_2+)+CO \qquad (2)$$

In the preferred embodiment, wherein the F/CO combination favors the formation of $COF_2$ upon quenching, the reaction of step (c) can be depicted as follows:

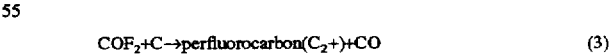

$$COF_2+C \rightarrow \text{perfluorocarbon}(C_2+)+CO \qquad (3)$$

TFE is a preferred perfluorocarbon and is preferably present as at least 50 mol % of the perfluorocarbon, more preferably at least 90 mol %.

The CO byproduct is used to form part, but preferably essentially all of the CO feed to the metal fluoride (or other fluorine-containing compound)/CO reaction step. The oxygen for forming CO in equations (2) and (3) comes from $COF_2$ or moieties favoring $COF_2$ being present in the gaseous reaction mixture of step (a) and present in the feed to step (c). By material balance, the amount of CO formed in the carbon reaction step can be the same amount of CO consumed in the metal fluoride/CO reaction step (a).

When the metal fluoride (or other fluorine-containing compound)/CO reaction is carried out under exposure to dissociation energy which produces a reaction temperature less than needed for the carbon reaction step, or when the quenching of the gaseous reaction mixture of step (a) reduces the temperature too low, then heat will be needed to achieve the carbon reaction temperature.

The desired fluorocarbons are separated from the reaction product by any variety of methods known to those skilled in the art, including distillation, absorption, or adsorption. Along with the recycling of CO to step (a), undesired fluorocarbons, any unconverted metal fluoride or other fluorine-containing compound, and $COF_2$ can be recycled to the appropriate reaction step of the process. For example, when $CF_4$ is produced as a byproduct of the process, this one-carbon-atom fluorocarbon can be recycled to step (a) or step (c), so that eventually the $CF_4$ will be converted to a desired perfluorocarbon having at least 2 carbon atoms, whereby the process of the present invention is referred to herein as being for the preparation of perfluorocarbon having at least two carbon atoms. The expression "one-carbon-atom perfluorocarbon" as used herein excludes $COF_2$.

EXAMPLE 1

The desired reaction sequence in the first reaction step is as follows:

$$SiF_4 + 2CO \rightarrow Si + 2COF_2$$

The feed in this Example, however, has 400% molar excess of carbon monoxide to help drive the reaction to the desired reaction products shown above. Thus, on a weight basis, 280 g/min of CO are fed between the electrodes of a plasma reactor (e.g., Westinghouse MARC® 3 plasma torch) at atmospheric pressure and generating a temperature of about 6000° C. to form a plasma flame of the CO extending downstream from the electrodes. Into this flame are injected 104 g/min of preheated gaseous $SiF_4$ to thereby be mixed with the CO in the flame. The flame extends into a cooled graphite reactor. The temperature in the flame is about 5000° C. The resultant gaseous mixture is quenched to about 1500° C. using a cooled surface at a quench rate exceeding 10000° C./sec, and a liquid product separates from the gaseous reaction mixture. This liquid product is removed from the reactor at a rate of 26 g/min. On solidification at ambient temperature (15°–20° C.), elemental analysis by ESCA shows the composition of the product to be as 89 wt % Si, 6 wt % oxygen, and 5 wt % fluorine, with the exiting fluorine being a complex (called SiF in Table 1) with the silicon metal. This reaction product can be refined to obtain Si at higher purity. The remaining hot gaseous mixture has a flow rate of 358 grams per minute of which 239 grams per minute is unconverted CO, 19 grams per minute is unconverted silicon tetrafluoride, along with 90 grams per minute of $COF_2$ and 10 grams per minute of $CF_4$. This analysis is determined by using a calibrated infrared spectrometer unit. Thus, 82% of the $SiF_4$ is converted and the yield to $COF_2$ and usable $CF_4$ is almost 98%. Similar results are obtained when the gaseous mixture is quenched at a rate exceeding 10000° C./sec. to 600° C. using a cooled quench surface, in which case a solid product separates from the gaseous mixture at a rate of 26 g/min. With additional cooling to ambient temperature (15°–20° C.), elemental analysis by ESCA gives a result similar to that obtained on the liquid product described above.

The reaction sequence in the next step of the process of this Example has the following desired reaction sequence:

$$COF_2 + 2C \rightarrow 3CF_2 + CO$$

The $CF_4$ obtained in the first step of this reaction, is included in the feed to the carbon-reaction step. The desired immediate reaction product of this step is shown as $CF_2$: which on quenching forms TFE, HFP and other desirable fluorocarbons. Presence of TFE in the quenched product confirms the presence of $CF_2$: in the reaction product. The feed mixture to this step is reheated from 1500° C. (or from 600° C., as the case may be) to 2500° C. and passed through a bed of carbon to form a second gaseous reaction mixture. Upon quenching of this second reaction mixture to ambient temperature at a rate exceeding 10000° C./sec through a cooled bed of carbon, the resultant reaction mixture analyzes as follows:

| Component | Grams/minute |
|---|---|
| CO | 270 |
| $SiF_4$ | 19 |
| $COF_2$ | 18 |
| $CF_4$ | 4 |
| $CF_2=CF_2$ | 54 |
| $CF_3CF=CF_2$ | 2 |
| $C_2F_6$ | 3 |
| Misc. FCs | 1 |
| Total | 371 |

To obtain this analysis, two analytical procedures are used. A calibrated infrared spectrometer (IR) is first used to calculate the amount of CO, $SiF_4$, $COF_2$, and $CF_4$ in the total gas stream. The specific wave numbers ($cm^{-1}$) used to identify these compounds for quantitative analysis are as follows: CO=2172, $SiF_4$=1030, $COF_2$=1955 and $CF_4$=1281. A second analytical procedure (gas chromatography) is used to quantitatively identify the remaining fluorocarbons (TFE, HPFP, $C_2F_6$, and miscellaneous fluorocarbons). In accordance with this second procedure, a sample stream is first double scrubbed in water. This scrubbing action removes the $SiF_4$ and $COF_2$ by the reactions shown below:

$$3\ SiF_4 + 2\ H_2O \longrightarrow 2\ H_2SiF_6\ (in\ H_2O\ solution) + SiO_2$$
(precipitate)

$$COF_2 + H_2O \longrightarrow 2\ HF\ (in\ H_2O\ solution) + CO_2$$

After scrubbing, the sample stream is dried over calcium sulfate and then a small amount of this gas is injected into a gas chromatograph for additional analysis. A Hewlett-Packard 5880A series gas chromatograph is used for this analysis. A 20 foot long, 1/8th inch diameter, stainless steel column (from Supelco, Inc.) packed with 60/80 mesh Carbopack® B, with 1% SP-1000, is used to separate the residual components of the sample stream. After a sample is injected into the gas chromatograph, the temperature on the column is held constant for 5 minutes at 40° C. and then the temperature is increased to 180° C., at a rate of 20° C./minute. The total elapsed time for an analysis is usually 20 minutes. The gas chromatographic results can be converted into weights and weight percents. These same analytical methods are used to obtain other analysis results disclosed in the Examples.

The combined carbon consumption rate, primarily from the bed of carbon but some from the cooled bed of carbon (quench), is 14 g/min. The above analysis shows that about 80% of the $COF_2$ is converted to other fluorocarbons, while about 60% of the $CF_4$ is converted. The yield to TFE is 66% based on converted $SiF_4$, without any benefit of recycle of $SiF_4$, $COF_2$, $CF_4$ and the miscellaneous fluorocarbons. Upon separation and purification, the CO formed in the second reaction step can be recycled to the electrodes of the first reaction step and the unreacted $SiF_4$ can be recycled to the plasma flame of the first reaction step. Any of the undesirable perfluorocarbons, including the miscellaneous FCs could be recycled to the plasma flame. The $CF_4$ could be recycled to the plasma flame or to the reaction step over the carbon bed and the $COF_2$ can be recycled to the latter. The amount of CO formed in the second reaction step is 10 g/min less than the CO feed to the first reaction step; eight of this g/min loss of oxygen is accounted for by the unreacted $COF_2$, leaving only about 2 g/min of oxygen available for formation of $SiO_2$ in the first reaction step. This amount of oxygen can be added to the carbon bed of the second reaction step to form CO at the reaction temperature, so that the amount of CO formed in the second step can be the entire amount desired as the feed to the first reaction step.

EXAMPLE 2

The desired reaction sequence of the first reaction step of this Example is as follows:

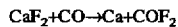

$$CaF_2 + CO \rightarrow Ca + COF_2$$

The plasma reactor (torch) and the cooled graphite reactor described in Example 1 are used in this Example. Again a 400% excess of CO is used to drive the reaction to the desired products. Thus, on a weight basis, 135 g/min of CO is fed to the arc electrodes at atmospheric pressure and heated to about 6000° C. Additional CO (about 5 g/min) is used to help aspirate the gravity feed of 78 g/min of powdered preheated $CaF_2$ into the plasma flame downstream from the electrodes, wherein the temperature is about 5000° C. The resultant gaseous reaction stream is quenched at a rate exceeding 10,000° C./sec to a temperature of 500° C., and a solid product at the rate of 48 g/min is removed from the gaseous reaction mixture. Upon cooling to ambient temperature, this solid product is analyzed to contain 62 wt % Ca, 32 wt % $CaF_2$, and 6 wt % CaO. The $CaF_2$ in this solid product accounts for 20% of the $CaF_2$ feed to the reactor, whereby 80% of this feed is converted in the reactor.

The exit gases, at 170 grams per minute contain 118 grams per minute of CO, 2 grams per minute of $CF_4$, and 50 grams per minute of $COF_2$.

The desired reaction sequence for the next reaction step of this Example, is as follows:

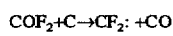

$$COF_2 + C \rightarrow CF_2: + CO$$

The $CF_4$ obtained in the first reaction step is also included in the feed to this reaction step. The exit gases from the first reaction step are reheated and fed to the hot carbon bed and quenched as done in the second reaction step of Example 1, except that the quench rate is slightly slower. The resultant second gaseous reaction mixture has the following composition:

| Component | Grams/minute |
|---|---|
| CO | 135 |
| $COF_2$ | 10 |
| $CF_4$ | 1 |
| $CF_2=CF_2$ | 24 |
| $CF_3CF=CF_2$ | 2 |
| $C_2F_6$ | 4 |
| Misc. FCs | 1 |
| Total | 178 |

The carbon consumption rate for this Example is 8 g/min. The above analysis shows that 80% of the $COF_2$ is converted and only 55% of the $CF_4$ is converted. The yield of TFE in this process is 59.1% based on the converted $CaF_2$, without the benefit of recycle of $COF_2$, $CF_4$, and miscellaneous fluorocarbons. The slightly slower quench rate favored the formation of a greater proportion of HFP and $C_2F_6$ compared to TFE.

The following tables tabulate the material flow rates for Examples 1 and 2.

TABLE 1

Flow Rates in G/Min for Example 1

| Component | Plasma Feed | Liquid Product | Exit Gases | Carbon System Feed | Product Gases |
|---|---|---|---|---|---|
| CO | 280 | | 238.9 | 238.9 | 269.5 |
| $SiF_4$ | 104 | | 19.0 | 19.0 | 19.0 |
| $COF_2$ | | | 90.3 | 90.3 | 18.1 |
| $CF_4$ | | | 10.0 | 10.0 | 4.0 |
| $SiO_2$ | | 3.0 | | | |
| Si | | 19.6 | | | |
| SiF | | 3.2 | | | |
| Carbon | | | | 13.5 | |
| TFE | | | | | 54.1 |
| HFP | | | | | 2.5 |
| $C_2F_6$ | | | | | 3.4 |
| Misc. Fluoro | | | | | 1.1 |
| Total | 384 | 25.8 | 358.2 | 371.7 | 371.7 |

TABLE 2

Flow Rates in G/Min for Example 2

| Component | Plasma Feed | Solid Product | Exit Gases | Carbon System Feed | Product Gases |
|---|---|---|---|---|---|
| CO | 140 | | 117.9 | 117.9 | 134.7 |
| $CaF_2$ | 78 | 15.6 | | | |
| $COF_2$ | | | 49.6 | 49.6 | 9.9 |
| $CF_4$ | | | 2.1 | 2.1 | 0.9 |
| Calcium | | 30.0 | | | |
| CaO | | 2.8 | | | |
| Carbon | | | | 7.8 | |
| TFE | | | | | 23.6 |
| HFP | | | | | 2.6 |
| $C_2F_6$ | | | | | 4.5 |
| Misc. Fluoro | | | | | 1.2 |
| Total | 218 | 48.4 | 169.6 | 177.4 | 177.4 |

In each of the experiments described in Examples 1 and 2, the gaseous reaction mixture can be quenched to ambient temperature and then reheated to perform the second step.

EXAMPLE 3

A different plasma reactor was used in the experiment forming the subject matter of this Example. The plasma torch is a Metco (Model MBN) torch and this torch is mounted across the top opening of a water-cooled copper cylinder having an inner diameter of 2.54 cm and a length of 5.08 cm, to form the plasma reactor. The pressure within the reactor is maintained at 61 torr. The outlet end of the reactor communicates with a water-cooled heat exchanger. The heat exchanger can be by-passed in favor of a reactor containing a gas-permeable bed of carbon particles heated to about 2500° C., which in turn, communicates with a quench chamber for quenching gas products to ambient temperature.

The feed gas to the plasma torch consists of argon, fed to the torch at a flow rate of 7.5 liters (STP)/min, the torch operating at a current of 450 amps and at 33 volts, producing a power input of 14.8 KW. The argon plasma flame extends into the copper cylinder (reactor) via the inlet end of the reactor, and energy balance calculations indicate the temperature of the plasma flame (bulk gas temperature) at the inlet end are about 10,000° K. At the reactor inlet, $SiF_4$ is injected into the plasma flame at 1–9 liters (STP)/min through injection nozzles sized to promote sonic velocities and good mixing of the $SiF_4$ in the plasma flame, to promote dissociation of the $SiF_4$ and formation of free fluorine. CO is injected into the reactor at the rate of 30 liters (STP)/min 5.08 cm downstream from the reactor inlet to react with the free fluorine and to quench the plasma flame to favor the formation of $COF_2$ rather than $CF_4$. The CO is at room temperature when injected into the reactor, so that simultaneous with the reaction between CO and F, he CO together with the water-cooled reactor wall rapidly quenches the resultant gaseous reaction product.

The gaseous reaction product is quenched to ambient temperature (15°–20° C.) for the purpose of infrared analysis, and this quenching is accomplished by passing the product gas through the water-cooled heat exchanger. Samples of the product gas are collected in bags of Tedlar® polyvinyl fluoride for infrared analysis. Fluorocarbon yields in the product gas are 94 mol % $COF_2$ and 6 mol % $CF_4$.

The plasma reaction is continued except that the gaseous reaction product by-passes the heat exchanger and flows into the reactor containing the heated carbon bed. The resultant gaseous reaction product is then quenched to ambient temperature and analyzed by infrared, indicating that the fluorocarbon yield is greater than 70% TFE.

What is claimed is:

1. Process for the preparation of perfluorocarbon containing at least two carbon atoms, comprising feeding fluorine-containing compound having a molecular weight greater than 20 and gaseous CO to a reaction zone wherein the fluorine-containing compound is split apart to liberate fluorine from said fluorine-containing compound and obtaining a gaseous reaction mixture which contains said fluorine and said CO, reacting said reaction mixture with carbon at a temperature of at least 1500° C. to obtain a gaseous reaction product, rapidly cooling said gaseous reaction product to obtain said perfluorocarbon as a result thereof, and recovering said perfluorocarbon from said gaseous reaction product.

2. The process of claim 1 wherein said reaction zone is at an elevated temperature and said fluorine and CO are maintained in said gaseous mixture by cooling said mixture from the elevated temperature of said reaction zone.

3. The process of claim 2 wherein said fluorine-containing compound is metal fluoride and said gaseous reaction mixture contains metal from said metal fluoride.

4. The process of claim 3 and removing said metal from said gaseous reaction mixture prior to carrying out the reacting step.

5. The process of claim 3 wherein said gaseous reaction product of the reacting step contains said metal and said recovery of said perfluorocarbon in the recovery step includes recovery from said metal.

6. The process of claim 1 wherein the step of reacting with carbon to produce said gaseous reaction product produces CO and said CO is recycled to the feeding step.

7. The process of claim 2 wherein said process is carried out continuously and wherein heat is required for the reacting step, which heat includes heat recovered from the feeding step.

8. The process of claim 1 wherein the liberation of fluorine is caused by the energizing of said compound and said CO in said reaction zone at a temperature of at least 1500° C.

9. The process of claim 8 wherein said temperature is at least 3500° C.

10. The process of claim 9 wherein said reaction mixture is quenched to a temperature of 500° C. to 2000° C.

11. The process of claim 8 wherein the reaction temperature in the reacting step is at least 1500° C.

12. The process of claim 3 wherein said metal fluoride is silicon fluoride.

13. The process of claim 3 wherein said metal fluoride is calcium fluorosilicate.

14. The process of claim 3 wherein said metal fluoride is calcium fluoride or sodium fluoride.

15. The process of claim 3 wherein said metal is silicon.

16. The process of claim 1 wherein at least one molecule of CO is present for each two fluorine atoms provided by said fluorine-containing compound.

17. The process of claim 1 wherein at least 50 mol % of said perfluorocarbon is tetrafluoroethylene.

18. The process of claim 1 wherein unreacted fluorine-containing compound and/or CO are recycled to the feeding step.

19. The process of claim 1 wherein any one-carbon-atom perfluorocarbon present in said resultant reaction product is recycled to the reacting step.

20. The process of claim 19 wherein said one-carbon-atom perfluorocarbon comprises $CF_4$.

21. The process of claim 1 wherein the splitting apart of said fluorine-containing compound is by energizing said compound by forming a plasma in said reaction zone.

22. The process of claim 21 wherein the plasma is formed of at least one of said fluorine-containing compound and said CO, and when only one of these feed materials forms said plasma, said one feed material in the resultant energized state is then brought into contact with the other of said feed materials.

23. The process of claim 1 wherein inert gas is fed to said reaction zone, and said inert gas is energized therein and in the energized state is brought into contact with said fluorine-containing compound and said CO in said reaction zone.

24. The process of claim 1 wherein said fluorine and CO in said gaseous reaction mixture is capable of forming $COF_2$.

25. Process comprising contacting and reacting fluorine-containing compound with CO to form a gaseous reaction mixture which is capable of being quenched to form $COF_2$ and contacting and reacting said gaseous reaction mixture with carbon to form a second gaseous reaction mixture which is capable of being quenched to form perfluorocarbon which contains at least 2 carbon atoms and quenching said second gaseous reaction mixture.

26. The process of claim 25 wherein said fluorine-containing compound is metal fluoride and said first-mentioned gaseous reaction mixture contains metal liberated from metal fluoride, and removing said metal from said gaseous reaction mixture prior to said contacting and reacting with carbon.

27. The process of claim 25 wherein said contacting and reacting with carbon produces CO which is recycled to the first-mentioned contacting and reacting step.

28. The process of claim 25 wherein said perfluorocarbon is perfluoroolefin.

29. Process of reacting metal fluoride and CO by plasma excitation to form a gaseous reaction mixture which is capable of being quenched to $COF_2$ and reacting at least a portion of said gaseous mixture with carbon at a temperature of at least 1500° C. to form a second gaseous mixture which is capable of being quenched to form perfluorocarbon containing at least 2 carbon atoms and quenching said second gaseous reaction mixture.

30. The process of claim 26 wherein said perfluorocarbon is perfluoroolefin.

31. The process of claim 29 wherein said metal fluoride is heated to liberate fluorine therefrom for reaction with said CO and said metal is in the first-mentioned gaseous reaction mixture.

32. The process of claim 31 and recovering said metal from said first-mentioned or said second gaseous reaction mixture.

33. The process of claim 29 wherein said reaction of said metal fluoride with said CO occurs by plasma excitation and said first-mentioned gaseous reaction mixture is capable of being quenched to $COF_2$.

34. The process of claim 1 wherein said fluorine-containing compound is selected from the group consisting of metal fluoride and organic-fluorine containing compound.

35. The process of claim 34 wherein said organic fluorine-containing compound is $CH_4$ or $C_2F_6$.

36. The process of claim 34 wherein said metal of said metal fluoride is selected from the group consisting of elements in Groups IA, excluding hydrogen, IB, IIA, IIB, IIIA, IIIB, IVA, excluding nitrogen, VB, VIA, excluding oxygen, VIB, VIIB, and VIII of the Periodic Table.

* * * * *